(12) United States Patent
Horrobin et al.

(10) Patent No.: US 6,989,380 B2
(45) Date of Patent: Jan. 24, 2006

(54) TREATMENT OF PAIN

(75) Inventors: David Frederick Horrobin, Stirling (GB); Cari Loder, London (GB); Graham Cooper, Stirling (GB)

(73) Assignee: The WKK Trust, Kent (GB)

( * ) Notice: Subject to any disclaimer, the term of this patent is extended or adjusted under 35 U.S.C. 154(b) by 455 days.

(21) Appl. No.: 10/213,905

(22) Filed: Aug. 7, 2002

(65) Prior Publication Data

US 2002/0187958 A1 Dec. 12, 2002

Related U.S. Application Data

(63) Continuation of application No. 09/242,882, filed as application No. PCT/GB97/02295 on Aug. 27, 1997, now Pat. No. 6,451,788.

(30) Foreign Application Priority Data

Aug. 29, 1996 (GB) .............................. 9617990

(51) Int. Cl.
  *A61K 31/55* (2006.01)

(52) U.S. Cl. ...................... 514/212; 514/213; 514/217; 514/553; 514/559; 562/444; 562/445

(58) Field of Classification Search ................ 514/212, 514/52, 2, 213, 217, 553, 559; 530/300; 562/444, 562/445
See application file for complete search history.

(56) References Cited

U.S. PATENT DOCUMENTS

| 4,652,559 A | | 3/1987 | Szmuszkovicz | |
|---|---|---|---|---|
| 4,843,071 A | * | 6/1989 | Hohenwarter | ............... 514/217 |
| 4,431,670 A1 | | 9/2002 | Heller | |
| 6,451,788 B1 | * | 9/2002 | Horrobin et al. | ........... 514/221 |

FOREIGN PATENT DOCUMENTS

| WO | WO 96/11009 | * | 4/1996 |
|---|---|---|---|
| WO | WO 98/01157 | | 11/1998 |

OTHER PUBLICATIONS

File Embase on STN. An. No. 75125363. Kline et al. 'A Pattern of Antidepressive Effect of Tryptophan and Imipramine in Males & Females', 1974, 35/10, pp. 481–483. (abstract only).*

File Embase on STN. An. No. 78041313; Segawa, et al. "Effect of Lofepramine and other Antidepressants on the Uptake of 5 Hydroxytryptamine and Noradrenaline into Rat Brain Monoaminergic Neurons"; J. of Pharm. and Pharmac., 29(3): 139–142 (1977) [Abstract].

File Scisearch on STN. An. No. 94:4006, Max, M.B. "Antidepressant Drugs as Treatments for Chronic Pain–Efficacy and Mechanisms"; Advances in Pain Research and Therapy, 22: 501–515 (1995) [Abstract only].

File Embase on STN. An. No. 75125363, Kline et al. "A Pattern on Antidepressive Effect of Tryptophan and Imipramine of Males & Females"; *35(10)*: 481–483 (1974) [Abstract only].

Freedman, et al. "Vascular Headache: A Presenting Symptom of Multiple Sclerosis"; Canadian J. of Neurological Sciences, *16(1)*: 63–66 (1989).

Hooge, et al. "Trigeminal Neuralgia in Multiple Sclerosis"; Neurology, *45*: 1294–1296 (1995).

Brisman, R. "Trigeminal Neuralgia in Multiple Sclerosis"; Arch. Neurol., *44*: 379–381 (1987).

Scadding, Oxford Textbook of Medicine, OVP, 3936–3946 (1996).

Kost, et al. New England J. of Med., *335*: 32–42 (1996).

Galer, Neurology, *45 (Supp 9)*: S17–S25 (1996).

Okada, et al. "Effect of Methylcobalamin on Diminished Motor Nerve Condition Velocity in the Tibal Nerve of Poorly Controlled Diabetes"; Clin. Trials J., *22(6)*: 534–536 (1985).

Simon, et al. "Zur Behandlung Therapieresistenter Schmerzzustande Mit Hydroxocobalmin"; Med. Mschr., *28*: 466–468 (1974).

Calanca, "Hydroxytryptophane (Oxitriptan) an Association Avec les Antipreseurs Classiques): une Ulterieure Possibilite Therapeutique"; Schewiz. Rundsch. Med. Prax., 77: 47–50 (1988).

* cited by examiner

*Primary Examiner*—Bruce R. Campell
*Assistant Examiner*—Anish Gupta
(74) *Attorney, Agent, or Firm*—Dann, Dorfman, Herrell & Skillman, P.C.

(57) ABSTRACT

A method of treating pain by the co-administration of an antidepressant together with one or more precursors or inducers of neurotransmitters, particularly amino acids selected from L-phenylalanine, L-tyrosine, L-tryptophan and L-DOPA.

1 Claim, No Drawings

TREATMENT OF PAIN

CROSS-REFERENCE TO RELATED APPLICATIONS

This application is a continuation of U.S. application No. 09/242,882, filed Jan. 4, 2000, now U.S. Pat. No. 6,451,788 which is U.S. National Phase of International Application No. PCT/GB97/02295, filed Aug. 27, 1997, the entire disclosures of which are incorporated by reference herein.

FIELD OF THE INVENTION

The invention relates to the treatment of pain.

BACKGROUND

Pain is one of the most important and feared symptoms of disease. Pain can be broadly divided into three classes:

1. Pain with a clearly defined cause which activates a normal nervous system and which can be effectively treated by removal of the cause, and usually alleviated by analgesics such as non-steroidal anti-inflammatories and opiates. Examples are pain due to trauma, infection or pathology such as an invading cancer.

2. Pain which appears to originate in damage to the central or peripheral nervous system itself and which may persist long after the original cause of the damage has been removed. This type of pain is usually called neuropathic or neuralgic and has many causes. Any form of trauma or other damage to any peripheral nerve or to certain parts of the central nervous system may be followed by prolonged pain which may persist for months, years or decades. The damage may be caused by accidental or surgical injury, by metabolic disturbances such as diabetes or vitamin B12 or other nutrient deficiency, by ischaemia, by radiation, by autoimmune attack, by alcohol, by infections, especially viral infections, particularly with the herpes virus, by tumours, by degenerative diseases, or by unknown factors such as may be operative in trigeminal and other neuralgias. This is by no means an exhaustive list. These types of pain often respond poorly to treatment and patients suffering them have frequently been subjected to trials of many different drugs without success. The most consistent successes are perhaps achieved with antidepressant drugs of various types. A drug for temporal lobe epilepsy, carbamazepine, is sometimes effective in trigeminal neuralgia though not usually in other types of pain in this class.

3. Pain of indeterminate origin. Many pains cannot easily be classified into one or other of these types. It is not clear whether many headaches and migraines are in type 1 or type 2. Low back pain is also often difficult to define.

Any individual who is experiencing pain immediately wants it relieved. Fortunately pain of the first type can often be treated successfully although this is not always the case. Pain of the second and third types is often poorly responsive to existing methods of treatment and many patients have tried large numbers of drugs without real success. The problems of dealing with such pain have been well described in recent articles such as those by J. W. Scadding, pp 3936 to 3946 in the 3rd edition of the Oxford Textbook of Medicine, Oxford University Press, 1996; R. G. Kost and S. E. Straus in the New England Journal of Medicine 335: 32–42, 1996; and B. S. Galer in Neurology, 45, Supplement 9, S17–S25, 1996.

PRESENT WORK

We have unexpectedly found a new approach to treating pain, especially pain of the second and third types described above, which appears to be much more effective than treatments currently available. This involves the administration of an antidepressant and a neurotransmitter precursor or inducer. The antidepressant may be one of any of the classes of antidepressant, but particularly tri- and tetra-cyclic and related compounds, selective and non-selective monoamine oxidase inhibitors, selective serotonin reuptake inhibitors and any other classes of compound which are believed to exert their antidepressant action by enhancing the effects of the catecholamine or serotonin classes of neurotransmitter substances.

We have conducted a comprehensive literature search and can find no references to the combined administration of an antidepressant and a neurotransmitter precursor or inducer for the treatment of pain. In particular we can find no reference to the co-administration of lofepramine and L-phenylalanine in pain management. There are very many papers on the uses of antidepressants in pain, as illustrated by the three papers mentioned above, but none of these to our knowledge discuss the simultaneous coadministration of a neurotransmitter precursor or inducer.

Nevertheless we understand that another inventor, Dr. Andrew Worsley, has made a related invention and has filed for patent protection (U.K. 9614121.3 of $5^{th}$ Jul. 1996 and another application thereafter). Dr Worsley's discovery also relates to relief of pain by combinations of phenylalamine and antidepressants but relates specifically to pain originating from peripheral neuropathies and especially diabetic neuropathy. Pain resulting from specific peripheral nerve damage and specifically the pain of diabetic neuropathy, are therefore excluded from this application.

THE INVENTION

The invention is as set out in the claims herein but broadly lies in the use of an antidepressant drawn from one of the classes mentioned, together with one or more neurotransmitter precursors or inducers for the treatment of any type of pain but particularly for neuropathic pain and pain of uncertain origin, including headache, migraine and back pain. The actives may be administered together or separately but so as to be present in the body together.

The invention also extends to pharmaceutical compositions of an antidepressant and a neurotransmitter precursor or inducer when for the treatment of pain, and to methods of making pharmaceutical compositions for the treatment of pain, wherein the actives are an antidepressant and a precursor or inducer of a neurotransmitter, or one such active when the composition is for use in conjunction with administration of the other.

In addition to the two major components, such pharmaceutical preparations or compositions may also contain one or more of vitamin B12, folic acid, vitamin B6, tetrahydrobiopterin and other compounds required for normal nerve metabolism.

SPECIFIC FORMULATIONS

The antidepressant which we have found to be most effective is lofepramine but, as stated, any other antidepressant may be used. Among suitable neurotransmitter precursors are L-phenylalanine, L-tyrosine or L-DOPA of the pathway leading to the synthesis of dopamine, noradrenaline and adrenaline, or alternatively tryptophan of the pathway leading to serotonin. More than one may be administered although we have observed particularly good results with L-phenylalanine. In addition, various co-factors known to be important in the nervous system or in the biosynthesis of the neurotransmitters may also be administered. Such compounds include folic acid, vitamin B12, tetrahydrobiopterin and vitamin B6.

The preferred antidepressant in the formulations is, as stated, lofepramine, but any other antidepressant may be used, including imipramine, amitriptyline, nortriptyline, mianserin, trimipramine, clomipramine, protriptyline, fluvoxamine, pargyline, triazolopyridine, phenelzine, tranylcypromine, moclobemide, fluoxetine, maprotiline, sertraline, venlafaxine, dothiepin, doxepin, paroxetine, viloxazine and others. Likewise the preferred neurotransmitter precursor in the formulation is, as stated, L-phenylalanine but this may be replaced or supplemented by L-tyrosine, L-tryptophan or L-DOPA.

The actives may be formulated separately or together in any appropriate formulation known to those skilled in the art, using appropriate excipients if necessary. The compounds may be formulated in any appropriate way, such as tablets, capsules, powders, emulsions, other liquid formulations, parenteral formulations and topical formulations for transcutaneous, rectal or vaginal or other route of administration. The two or more compounds may be formulated separately but provided together in a single pack.

The antidepressant component of the formulation will be provided in a dose that is active in conjunction with the neurotransmitter precursor or inducer and appropriate to the specific antidepressant, and will be adjusted by the doctor in accordance with conventional principles. Lofepramine, for example, may be provided in a daily dose of from 30 to 300 mg but usually of from 70 to 140 mg. The doses of the neurotransmitter precursors can be more flexible but will be in the range of 1 mg to 20 g per day, preferably 50 mg to 5 g per day and very preferably 300 mg to 3 g per day.

COMPOSITION EXAMPLES

The following are suitable compositions for administration against pain.

Example 1

Capsules of 70 mg lofepramine and 500 mg L-phenylalanine, bd.

Example 2

Capsules of 1×70 mg lofepramine, 2×500 mg L-phenylalanine. bd.

Example 3

Capsules as in Example 1 for administration, bd, with the normal requirement of vitamin B12 weekly by injection.

Example 4

Capsules of 50 mg amitriptyline and 250 mg L-phenylalanine, bd.

CASE HISTORIES

The following illustrate treatment according to the invention.

A 46 year old man suffered from intractable trigeminal neuralgia of many years standing. He had tried innumerable approaches to treatment including cryosurgery, nerve decompression, carbamazepine, phenytoin, diazepam, morpine, a long series of non-steroidal anti-inflammatories, fluoxetine, methylprednisolone, multivitamins and minerals, and tricyclic antidepressants. None had provided more than transient relief for a few days, which both he and his doctors attributed to placebo effects. He then was treated with lofepramine, 70 mg bd, together with L-phenylalanine, 500 mg bd. Within two days his pain was relieved and he has now been free of pain for three months.

A 49 year old woman suffered from chronic headache of unknown origin, exacerbated by migraines every two weeks or so. A very wide range of medications, including antidepressants, had proved ineffective over a period of ten years. A combination of 50 mg bd amitriptyline plus 250 mg bd L-phenylalanine produced relief of the chronic headache within 48 hours and has prevented the development of any migraines over a period of two months.

A 34 year old man suffered chronic low back pain after a sports injury when he was 25. A variety of analgesics had produced partial relief but no long term freedom from pain. A surgical attempt at treatment had left him with pain worse than before. A combination of lofepramine 70 mg bd and 1 g of L-phenylalanine produced relief within 72 hours which has persisted for over two months.

In this description and in the claims, the disclaimer in relation to pain caused by specific peripheral neuropathies is made with the intention of delineating the present filings from those Dr Worsley is understood to have made; it is thus in respect only of the countries of his patent applications.

What is claimed is:

1. A method of treating pain selected from headache and migraine, but excluding pain caused by diabetic neuropathy or other specific peripheral neuropathies, by the co-administration of amitriptyline and L-phenylalanine.

\* \* \* \* \*